(12) United States Patent
Huang (10) Patent No.: US 10,159,605 B2
(45) Date of Patent: Dec. 25, 2018

(54) DRESSING

(75) Inventor: Min-Chang Huang, Taipei (TW)

(73) Assignee: COMPOSE ELEMENT LIMITED, Taipei (TW)

( * ) Notice: Subject to any disclaimer, the term of this patent is extended or adjusted under 35 U.S.C. 154(b) by 241 days.

(21) Appl. No.: 13/462,561

(22) Filed: May 2, 2012

(65) Prior Publication Data

US 2013/0072843 A1 Mar. 21, 2013

Related U.S. Application Data

(60) Provisional application No. 61/534,953, filed on Sep. 15, 2011.

(51) Int. Cl.
*A61F 13/02* (2006.01)

(52) U.S. Cl.
CPC ...... *A61F 13/0209* (2013.01); *A61F 13/0206* (2013.01); *A61F 13/0213* (2013.01); *A61F 13/0246* (2013.01)

(58) Field of Classification Search
CPC .............. A61F 13/0209; A61F 13/0213; A61F 13/022; A61F 13/0206; A61F 2013/00119; A61F 2013/00748; A61F 2013/00753; A61L 15/42; A61L 15/60; A61L 15/26; A61L 15/58
USPC ................. 602/41–59, 75; 604/180
See application file for complete search history.

(56) References Cited

U.S. PATENT DOCUMENTS

| | | | | |
|---|---|---|---|---|
| 2,687,723 A | * | 8/1954 | Stern | 602/75 |
| 5,160,328 A | * | 11/1992 | Cartmell | A61F 13/0203 523/111 |
| 5,599,289 A | * | 2/1997 | Castellana | A61F 13/023 128/853 |
| 5,939,339 A | * | 8/1999 | Delmore et al. | 442/149 |
| 7,678,716 B2 | * | 3/2010 | Yahiaoui | C08J 5/04 442/118 |
| 2009/0297587 A1 | | 12/2009 | Yang et al. | |
| 2010/0198177 A1 | * | 8/2010 | Yahiaoui et al. | 604/359 |
| 2013/0053747 A1 | * | 2/2013 | Lin | 602/45 |
| 2013/0138068 A1 | * | 5/2013 | Hu et al. | 604/368 |

FOREIGN PATENT DOCUMENTS

| | | |
|---|---|---|
| CN | 1562382 A | 1/2005 |
| CN | 2008101224381 | 10/2008 |
| EP | 0610056 A1 * | 1/1994 |

OTHER PUBLICATIONS

CN Patent app No. 2008101224381 is also published as US2009297587A1.

* cited by examiner

*Primary Examiner* — Kari Rodriquez
(74) *Attorney, Agent, or Firm* — Hannah M. Tien (57) ABSTRACT

A dressing, comprising an inner layer and an outer layer; wherein the inner layer and the outer layer are aligned with trimming at one side of edge. The inner layer comprises hydrogel and meltblown nonwoven, and the outer layer comprises polyurethane film and pressure sensitive adhesive film. The dressing increases watertight closure. It could be applied in circular wound covering.

1 Claim, 11 Drawing Sheets

DRESSING

FIELD OF THE INVENTION

The present invention relates to the field of medical dressing technology, specifically provides a dressing that can keep a suitable environment for wound healing, shorten the healing time, antiseptic and reduce the chances of being infected.

BACKGROUND OF THE INVENTION

According to recent scientific and statistical reports, the global trauma market is growing demand, especially in surgical trauma; the total people have exceeded 100 million per year and showed an upward trend year by year. People with trauma and lacerations caused by accidents are around 20 million per year. The number of burns is about 10 million people each year. People with ulcerative wounds caused by chronic diseases, diabetes and aging have been more than 30 million per year.

Because of the treatment needs and the popularity of endoscopic surgery, the risks caused by surgery have greatly reduced, but followed by the needs of better postoperative wound care and scar prevention. Currently there have been methods with the help of various advanced wound caring dressings, in order to shorten the healing time and eliminate scars.

The traditional dressings are made of natural plant fibers or animal hair materials such as gauze, cotton pad, wool, and all kinds of oiled gauzes. These dressings are only temporary covering materials that need to be replaced in a certain period of time. The study of wound dressings lets us grow scientific understanding of them. Studies have shown that: a better trauma dressing is to maintain a good environment for cell growth and healing at wound, to control and absorb exudates; breathable, moisture permeable and can prevent bacterial invasion; can closely stick to the surface of wounds; can carry and release the drug; also should have good tissue and blood compatibility that when taking it off from the wound surface, no adhesion and desquamation occurs; and also should have better mechanical properties and tensile strength, easy to use. In existing technology, such as published on Oct. 29, 2008 China patent application No. 200810122438.1 provided a preparation method for medical hydrogel bed dressing, and the patent published on Jan. 12, 2005 issue No. CN1562382A named "Water emulsion containing polyurethane-based hydrogel wound dressing and preparation method" is about a hydrogel as a base for medical dressing.

The global Muslim population in 2010 is 16 milliards, which is 23.4% of the total global population. The forecasted average growth rate of Muslim population is 1.5% in the next 20 years. There are about 10 million boys with circumcision requirement each year, reported by Pew Forum on Religion & Public Life, Washington, D.C. There are about 40 million new born baby boys each year, global statistics of United Nations. According to 28% circumcision requirement, the number of circumcision cases would be about 12 million. The global markets of circumcision postoperative care are about 126 million U.S. dollars.

BRIEF DESCRIPTION OF THE DRAWINGS

FIG. 3 is the schematic diagram of the hydrogel structure.
10 is the polyurethane film layer
20 is the pressure sensitive adhesive layer
30 is the meltblown nonwoven
40 is the hydrogel
50 is the interpenetrating polymer network
100 is the inner layer
200 is the outer layer

SUMMARY OF THE INVENTION

The present invention relates to a dressing, comprising an inner layer and an outer layer; wherein the inner layer and the outer layer are aligned with trimming at one side of edge.

DETAIL DESCRIPTION OF THE INVENTION

The present invention provides a dressing, comprising an inner layer and an outer layer; wherein the inner layer and the outer layer are aligned with trimming at one side of edge.

In one embodiment, the dressing increases watertight closure.

In another embodiment, the inner layer comprises hydrogel and meltblown nonwoven, and the outer layer comprises polyurethane film and pressure sensitive adhesive film; wherein the meltblown nonwoven and the hydrogel are laminated by UV curing to form an interpenetrating polymer network, part of fibers of the meltblown nonwoven are exposed and fit stably with the pressure sensitive adhesive film.

The present invention also provides a method of circular wound covering, which is applying the dressing at wound area by circular covering.

The dressing of the present invention provides less contact of skin and the pressure sensitive adhesive film, which reduces skin allergies. Moreover, it makes circular wound covering more easily. Circular wound covering could be achieved in horizontal or vertical direction.

EXAMPLES

The examples below are non-limiting and are merely representative of various aspects and features of the present invention.

Example 1

The Schematic Diagram of the Dressing

Figure 1:
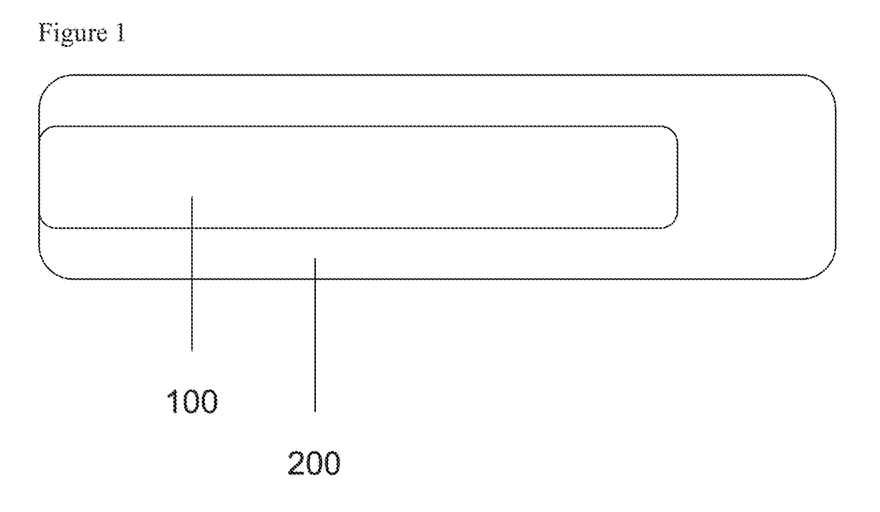
FIG. 1 is the schematic diagram of the dressing, vertical view.
100 is the inner layer
200 is the outer layer
Figure 2:
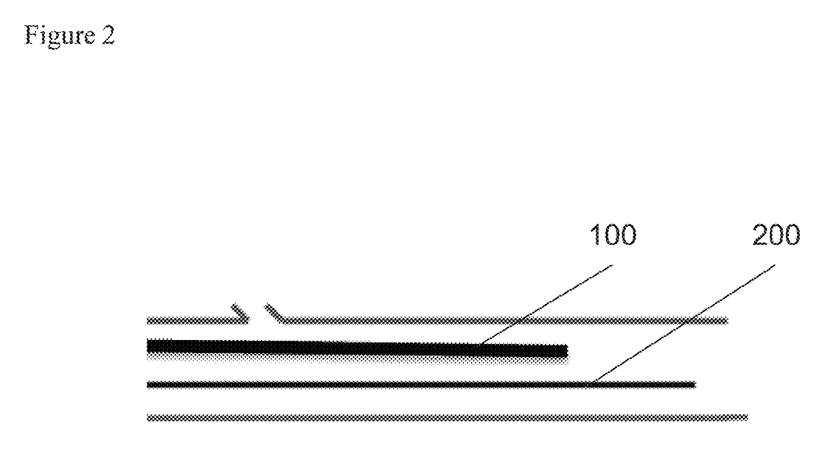
FIG. 2 is the schematic diagram of the dressing, side view.
100 is the inner layer
200 is the outer layer

As shown in FIGS. 1 and 2, the dressing, comprises an inner layer (100) and an outer layer (200); wherein the inner layer (100) and the outer layer (200) are aligned with trimming at one side of edge.

Example 2

The Hydrogel Structure

Figure 3:
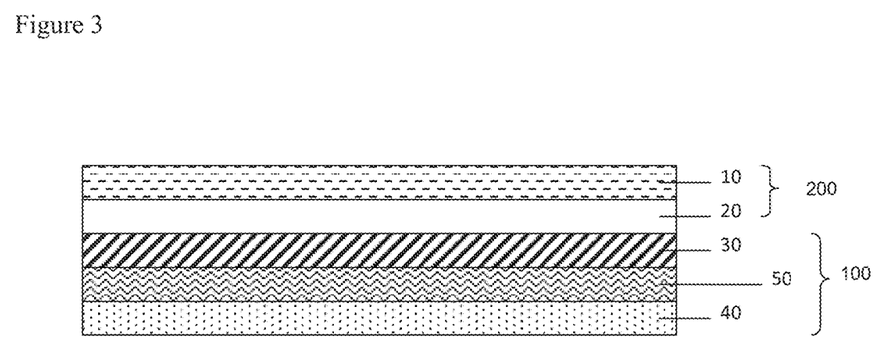

As shown in FIG. 3, the hydrogel structure comprises the polyurethane film layer (10), the pressure sensitive adhesive layer (20), the meltblown nonwoven (30) and the hydrogel (40) which formed an interpenetrating polymer network (50). The pressure sensitive adhesive layer (20) was coated on the polyurethane film layer (10). The meltblown nonwoven (30) and the hydrogel (40) were laminated by UV curing to make an interpenetrating polymer network (50), and part of the meltblown nonwoven fibers (30) were exposed and fit stably with the pressure sensitive adhesive layer (20) to form the hydrogel structure.

Example 3

The Hydrogel Formulation

The hydrogel was made by the steps as follows:
(a) providing a mixture comprising: (I) mixing the photoinitiator and the acrylic amide monomer to dissolve; (II) adding glycerol and mix to dissolve; (III) adding acrylic sulfonate monomer and mix to dissolve; (IV) adding glycerol and mix up.
(b) further providing a mixture comprising: (I) mixing the photoinitiator and the unsaturated double functional groups ester monomer.
(c) mixing up the mixture of step (a) and step (b).
(d) crosslinked polymerizing the mixture of step (c) by UV light irradiating to form the hydrogel.

The weight ratios of the above were

| | |
|---|---|
| Acrylic amide monomer | 15 to 30 units |
| Acrylic sulfonate monomer | 10 to 50 units |
| Glycerol | 15 to 45 units |
| Photoinitiator | 0.01 to 0.1 units |
| Unsaturated double functional groups ester monomer | 0.01 to 0.2 units |

Example 4

Tensile Test

For the hydrogel structure (LexiDerm) of the present invention, the polyurethane film layer and the hydrogel composites were examined based on ASTM D 412-98a Standard Test Methods for Vulcanized Rubber and Thermoplastic Elastomers-Tension, the results were as Table 1:

TABLE 1

| | Tensile strength and elongation test (Examining Unit: TTRI) | | | | | |
|---|---|---|---|---|---|---|
| Sample/ Number | Maximum strength Max (g) | Fracture strength (g) | 100% Modules (g/mm$^2$) | 300% Modules (g/mm$^2$) | Tensile strength (g/mm$^2$) | Elongation % |
| Polyurethane film layer/1 | 505.00 | 501.00 | 21.55 | 12.00 | 126.25 | 912.60 |
| Polyurethane film layer/2 | 1004.00 | 1004.00 | 25.56 | 13.43 | 251.00 | 1016.70 |
| Polyurethane film layer/3 | 1130.00 | 1130.00 | 24.34 | 11.98 | 282.50 | 1213.30 |
| Polyurethane film layer/4 | 661.00 | 647.00 | 26.26 | 12.85 | 165.25 | 950.05 |
| Polyurethane film layer/5 | 974.00 | 974.00 | 25.06 | 12.57 | 243.50 | 1111.70 |
| Polyurethane film layer/6 | 830.00 | 830.00 | 19.63 | 11.48 | 207.50 | 1113.10 |
| Hydrogel composites/1 | 354.00 | 321.00 | 43.27 | 19.69 | 141.60 | 925.63 |
| Hydrogel composites/2 | 304.00 | 256.00 | 33.15 | 17.68 | 121.60 | 886.30 |
| Hydrogel composites/3 | 289.00 | 263.00 | 26.56 | 13.75 | 115.60 | 935.05 |
| Hydrogel composites/4 | 304.00 | 258.00 | 29.08 | 16.03 | 121.60 | 881.20 |
| Hydrogel composites/5 | 287.00 | 221.00 | 29.59 | 17.43 | 114.80 | 907.02 |
| Hydrogel composites/6 | 413.00 | 306.00 | 37.56 | 21.75 | 165.20 | 959.95 |

Example 5

Breathability Test

For the hydrogel structure (LexiDerm) of the present invention, the polyurethane film layer and the hydrogel composites were examined based on JIS L 1096, the results were as Table 2:

TABLE 2

Breathability test (Examining Unit: TTRI)

| Number | Polyurethane film layer ($cm^3/cm^2/sec$) | Hydrogel composites ($cm^3/cm^2/sec$) |
| --- | --- | --- |
| 1 | 0.0035 | 0.0520 |
| 2 | 0.0028 | 0.0759 |
| 3 | 0.0035 | 0.0590 |
| 4 | 0.0030 | 0.0695 |
| 5 | 0.0028 | 0.0605 |
| 6 | 0.0025 | 0.0510 |

Example 6

Moisture Permeability Test

For the hydrogel structure (LexiDerm) of the present invention, the moisture permeability were examined based on JIS L 1099 A1 Calcium Chloride upright Cup test, the results were as Table 3:

Permeability ($g/m^2$ day)=(Second−First)*8488

TABLE 3

Permeability test (Examining Unit: TTRI)

| Sample/Number | First weight (g) | Second weight (g) | Result ($g/m^2$ day) |
| --- | --- | --- | --- |
| Hydrogel composites/1 | 230.138 | 230.893 | 6408.44 |
| Hydrogel composites/2 | 230.914 | 231.58 | 5653.008 |
| Hydrogel composites/3 | 230.718 | 231.388 | 5686.96 |
| Hydrogel composites/4 | 238.172 | 239.04 | 7367.584 |
| Hydrogel composites/5 | 230.423 | 231.124 | 5950.088 |
| Polyurethane film layer/1 | 227.869 | 227.963 | 797.872 |
| Polyurethane film layer/2 | 234.092 | 234.198 | 899.728 |
| Polyurethane film layer/3 | 226.27 | 226.373 | 874.264 |
| Polyurethane film layer/4 | 224.309 | 224.417 | 916.704 |
| Polyurethane film layer/5 | 228.073 | 228.179 | 899.728 |

Example 7

Absorption Rate

For the hydrogel structure (LexiDerm) of the present invention, the absorption rate were examined. The hydrogel were weighted and put it into 25° C., pH=7.4 PBS, after fully swelled, the surface water was wiped out and the hydrogel were weighted. The hydrogel were removed every time interval and were weighted till the weight of the hydrogel stopped changing. The absorption rate was measured by the change of the hydrogel weight, the swelling rate %=[(weight of the wet hydrogel−weight of the original hydrogel)/weight of the original hydrogel]×100%, the results are as FIG. 2.

Example 8

Wound Healing Test

Materials and Methods
(1) Test Objects
Gauze Control Group
The hydrogel structure of present invention experimental group (LexiDerm)
(2) Experimental Animals
Three animal strains of LYD 2 months old pigs that have passed the examination of experimental animal and Management Group of Taichung veterans general hospital (Number: La99736).
(3) Test Group
Animals were divided into two groups, Day 14 (three pigs) and Day 31 (one pig). Every animal had three 3 cm×3 cm all skin excision wounds on left and right side of the back respectively, then giving the control or experimental dressings respectively.
(4) Applying Methods
Applied the experimental or control substances directly on the wound on animals' back, and changed the substances every 3-5 days.
(5) In Vivo Animal Experiments
Experiments carried out on 2 months old LYD three strains of pigs as experimental animals. Experimental equipments included shaving knife, autoclaved with high temperature and pressure surgical instruments (ratio scale, hole towel forceps, scissors, tweezers, clamps, scalpel and needle holder) and consumables (sterile hole towel, gauze, cotton, tincture of iodine, alcohol and sutures), the procedures were as follows:
Each pig was giving leading anesthesia by ketamine (20 mg/kg) and xylazine (2 mg/kg), then by 1.0-2.0% isoflurane to maintain anesthesia. After shaving the back, sterilize with 70% Alcohol first, then with Betadine and covered with sterilized hole towels. Six 3 cm×3 cm all skin excision wounds with the depth to panniculus carnosis were created by scalpel. Covered the wounds with experimental or control dressings then with a layer of gauze and wrapped the wounds with elastic bandages or sutures to prevent infection caused by the broken of the dressings. Cleaned the wounds every 3-5 days after the surgery, changed new experimental or control dressings and then re-bandaged and fixed by the above methods. Postoperative care: In first 1-2 days, conducted postoperative analgesia by carprofen 2 mg/kg to relieve pain.
As mentioned above, the pigs should be fed separately, free to water and feed regularly after the operation. The experiments were recorded by day and evaluated the pigs as follows on Day 3, 7, 10, 12 after the operation. Clinical wound assessment—observed the skin and wound healing process. Record the dressing binding situation on the pigs separately, the amount of secretion, the situation of the wound surrounding tissue, the growth situation of the wound and the changing difficulty of the dressings. In addition to text recording, took pictures for comparison and finally arranged and analyzed the results. Wound healing promoting assessment—put a ratio scale and took pictures of the wounds on each dressing changing point. Calculated the wound area after the correction of graphics software Image Pro Plus 4.5 by the ratio scale, as shown in FIG. 3.

Figure 4:
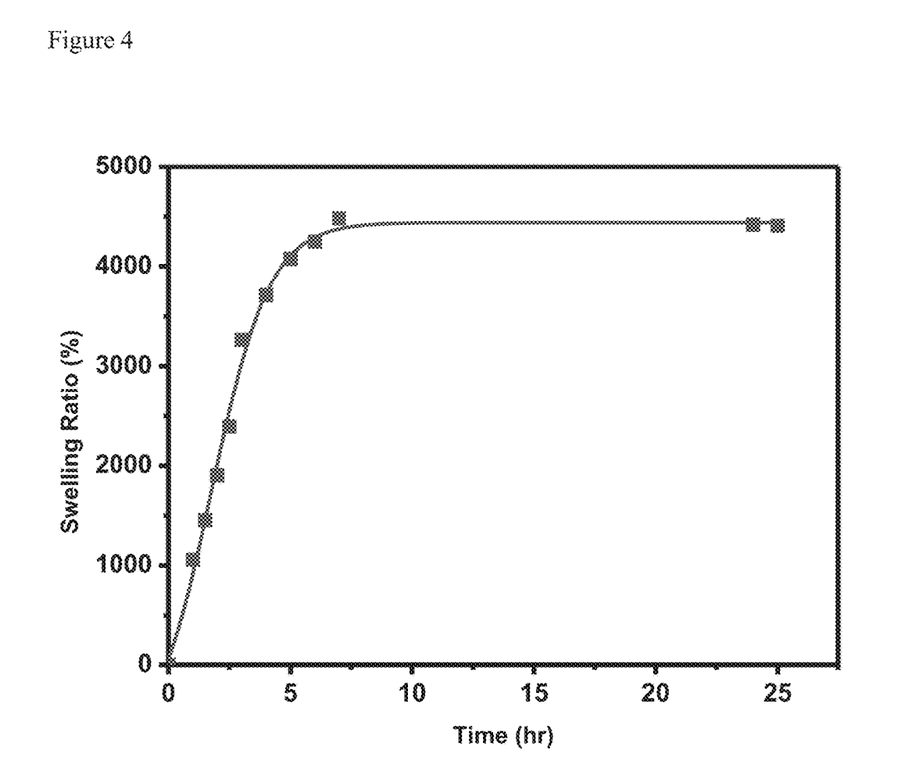
FIG. 4 is the swelling ratio of the hydrogel (%).

Histological assessment—took out the normal tissue together with the implanted samples and underwent histopathological biopsy (if required). 14 days after the surgery, took 5 mm wedge biopsies, need to include the dressing, granulation tissue, connective tissue and the muscle below. Fix tissues in formaldehyde first, then underwent dehydrate, embedding, de-wax, slice and stained with H & E and picro-Sirius red. Observe the interaction of epithelial cells, dermal cells, neovascularblasts, inflammatory cells and fibroblasts to assess wound healing.

control group was mainly the distortion of the wound and few skin tissues were formed. However, in the experimental group, there were more new skin tissues formed, but the newly formed skin tissues of the wound were smooth (FIG. 4, day 28).

(3) Postoperative Wound Promoting Healing Assessment

Figure 5:
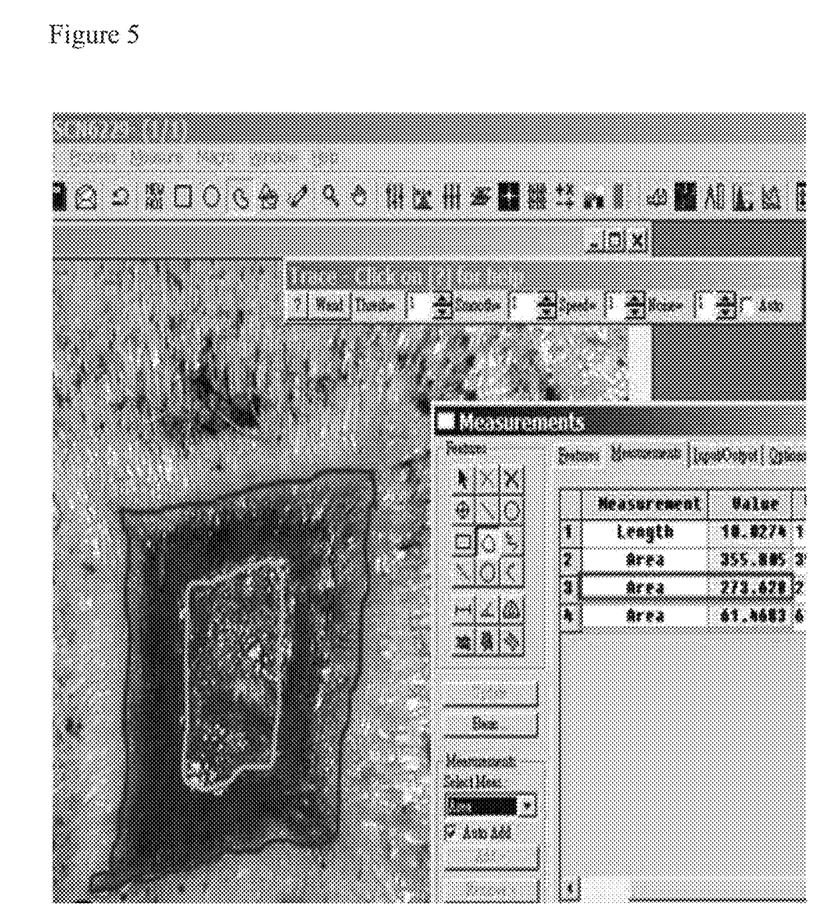
FIG. 5 is the wound area calculated by the software Image Pro Plus 4.5.

After quantitative analysis of wound area, we could see the wounds were significantly reduced in the experimental group compared to gauze control group on day 6 of dressing applied (FIG. 5 and Table 4).

TABLE 4

| Group | 0 day | 3 day | 6 day | 9 day | 12 day | 14 day |
|---|---|---|---|---|---|---|
| Control | 100 ± 0.0 | 94.0 ± 13.5 | 81.0 ± 9.6 | 45.4 ± 9.7 | 25.0 ± 6.3 | 17.2 ± 6.9 |
| LexiDerm hydrogel | 100.0 ± 0.0 | 100.1 ± 9.9 | 69.4 ± 11.2 | 26.6 ± 5.3 | 15.0 ± 4.6 | 11.0 ± 4.8 |

Scoring Standard:

Epidermis growing score: 0—No growth, 1—The growth of epidermis is smaller than ⅓ of the wound, 2—The growth of epidermis is between ⅓ and ½ of the wound, 3—The growth of epidermis is between ½ and ⅔ of the wound, 4—The growth of epidermis is more than ⅔ of the wound or completely healed.

Granulation score: 0—No growth of granulation tissue, 1—Loose growth of granulation tissue, 2—Dense growth of granulation tissue, 3—Connective tissue formed. Inflammation score: 0—Severe inflammatory response (large infiltration of neutrophils and lymphocytes), 1—Moderate inflammatory response (multi infiltration of lymphocytes), 2—Mild inflammatory response (small infiltration of lymphocytes), 3—No inflammatory response (no infiltration of lymphocytes).

Results:

(1) Postoperative Clinical Symptoms and Wound Observation Assessment

The first 1 to 2 days after pigs were conducted whole skin excision, giving them Capricorn 2 mg/kg for postoperative pain relieving by the principles of human experiments. During the experiment, pigs didn't show biting the wound portion and no dressing falling or frayed. On the dressing changing day, 3 and 6 days after the surgery, the dressings could not fully absorb the wound exudates and there were large amounts of exudates flowing out around the wounds in experimental and gauze control groups. The amounts of exudates were significantly reduced on the dressing changing day, 9 days after the surgery. In the adhesion condition between dressings and wounds, the gauzes adhered to the wound tissues easily and needed to rinse with saline solution to take them out during the experiment in the control group, but the dressings of the experimental group didn't have this situation.

(2) Postoperative Wound Healing Visual Assessment

The sizes of the wounds after conducted whole skin excision in pigs were between 28.72 to 32.52 mm$^2$. 6 days after dressings were applied; there was a little new skin tissue formed on the edge of the wound in the experimental group (FIG. 4, day 6). 12 days later, the wounds in each group were significantly reduced and the wound shapes were square and smooth. The newly formed skin tissue covered more than ½ of the wound in the experimental group on day 20. 28 days after dressings were applied; almost all the wounds had healed. The healing of the wounds in the gauze The percentage of the remaining wound area to the original area after applying the dressings 14 days (%).*: P<0.05, : P<0.01, *: P<0.001 Compared to the control group. Control (n=3), LexiDerm hydrogel (n=9).

(4) Histological Assessment of the Wound 14 Days after Applying Dressings

Figure 6:
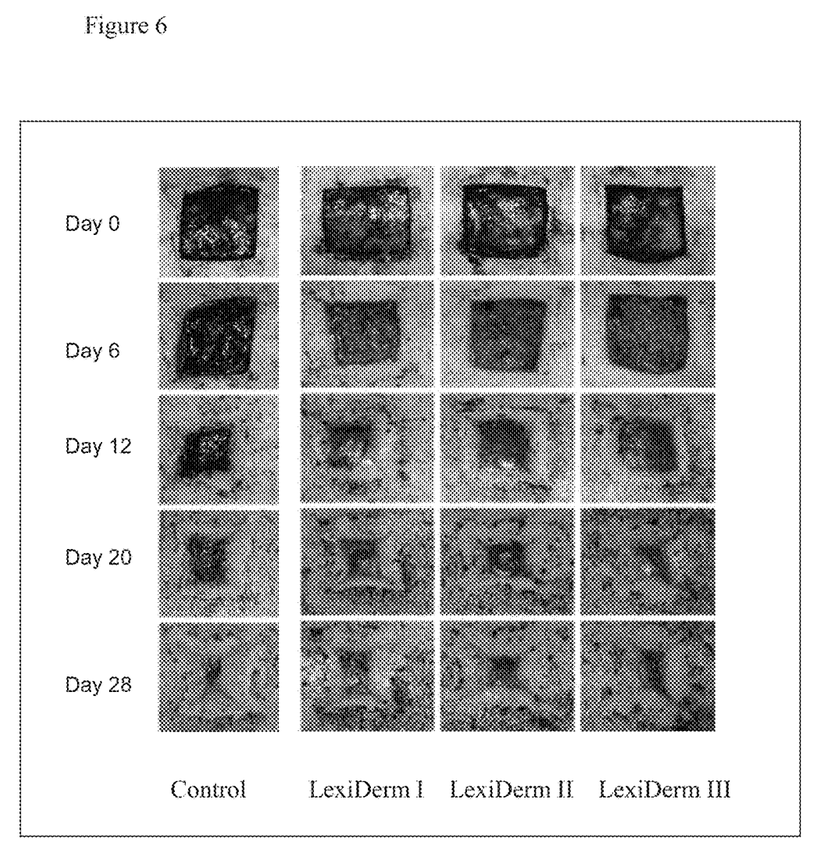
FIG. 6 is the appearance of the wound on different timing after the dressings are applied.
Figure 7:
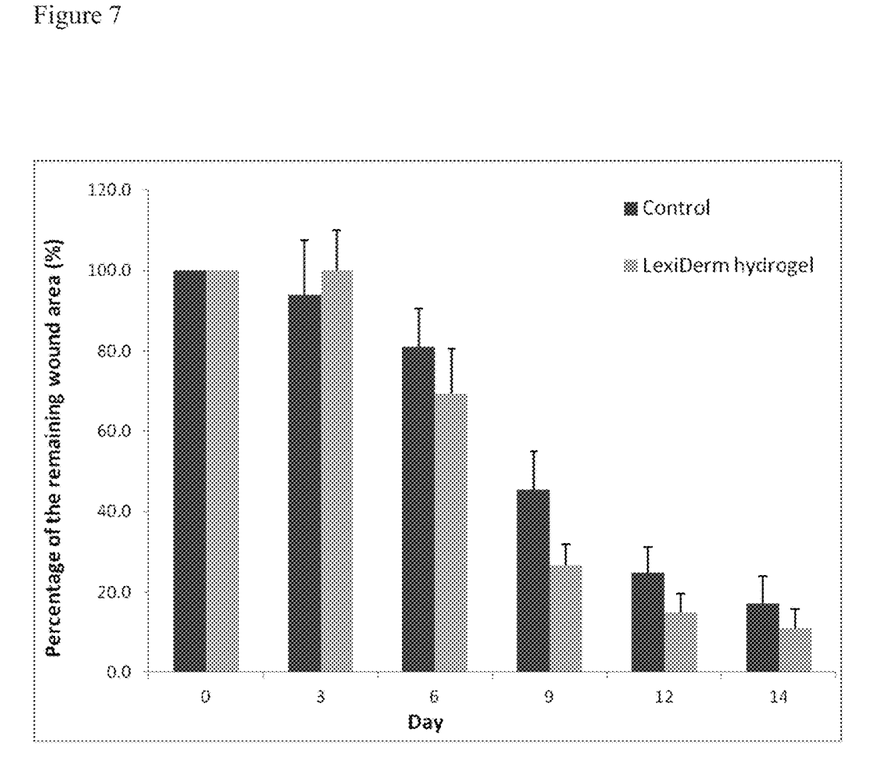
FIG. 7 is the percentage of the remaining wound area (%) after applying the dressings 14 days.
Figure 8:
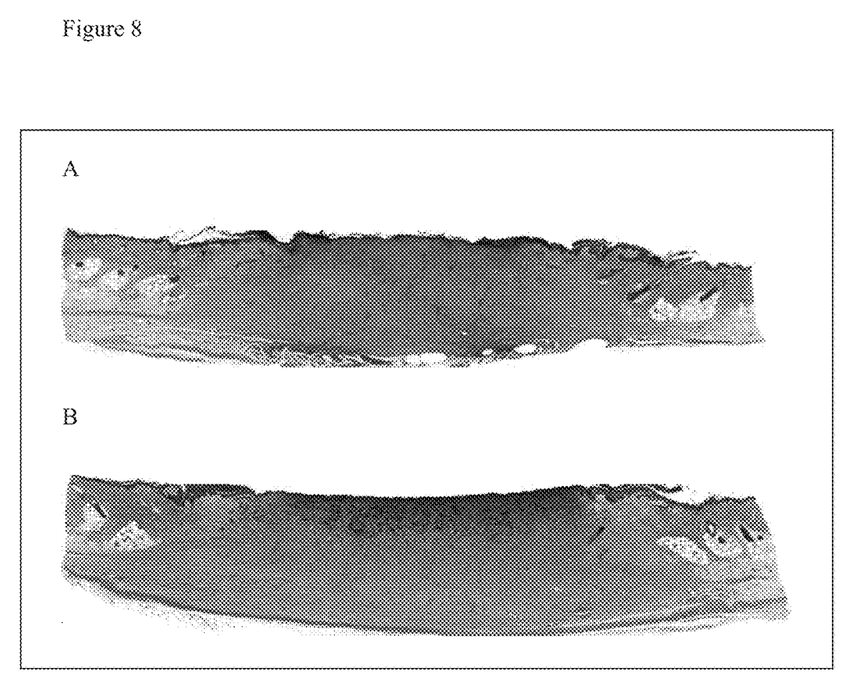
FIG. 8 is the representative figures of epidermal growth after applying the dressings 14 days. A represents the control group. B represents LexiDerm Hydrogel Dressing.
Figure 9:
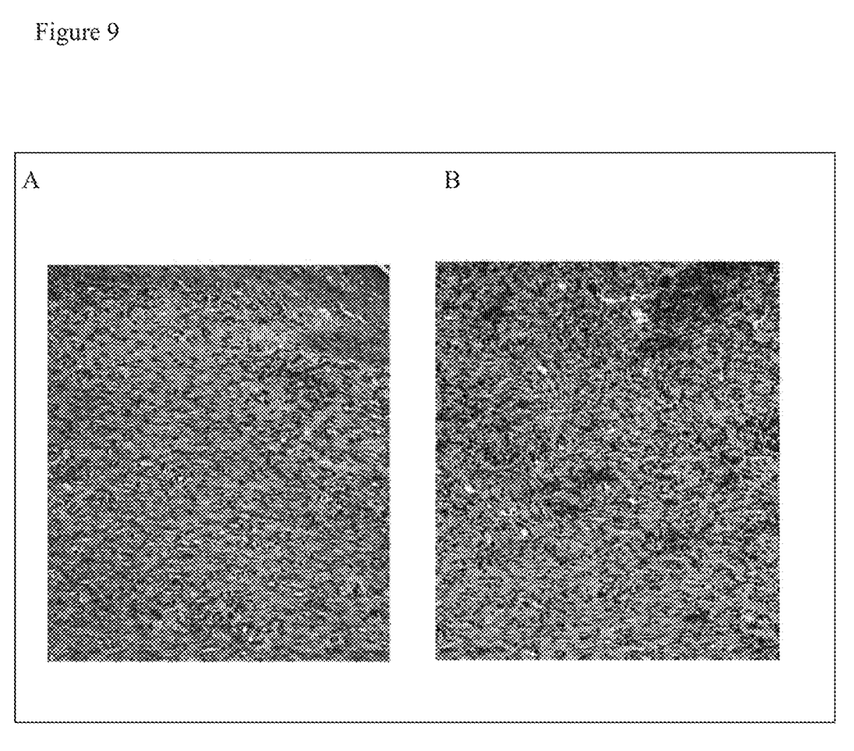
FIG. 9 is the representative figures of granulation growth and Inflammation after applying the dressings 14 days. A represents the control group. B represents LexiDerm Hydrogel Dressing.
Figure 10:
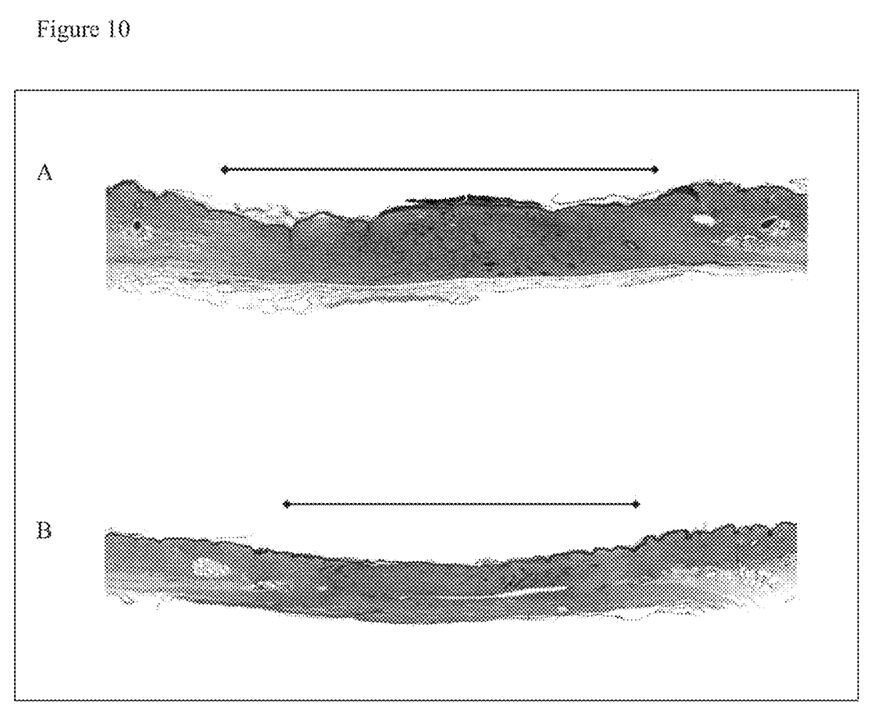
FIG. 10 is the representative figures of epidermal growth after applying the dressings 31 days. A represents the control group. B represents LexiDerm Hydrogel Dressing.
Figure 11:
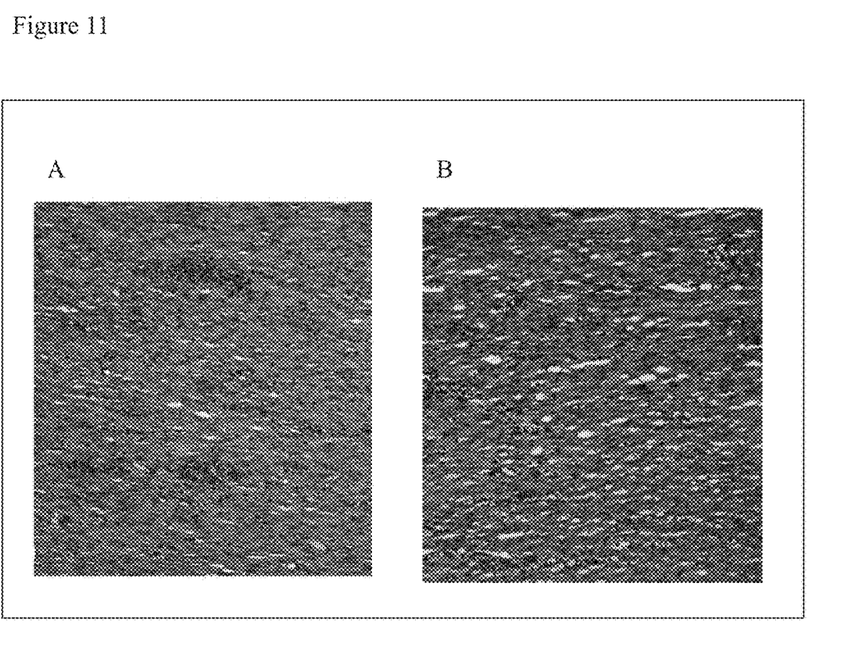
FIG. 11 is the representative figures of granulation growth and Inflammation after applying the dressings 31 days. A represents the control group. B represents LexiDerm Hydrogel Dressing.

Epidermis growing score: In the gauze control group, the growth of epidermis was near ⅓ of the wound and the score was 1. In other experimental groups, the growth of epidermis was between ⅓ and ½ of the wound, and the score was 2. The growth of epidermis in the experimental group was better than in the gauze control group (FIG. 6). Granulation score: The growth of granulation tissue in gauze control and experimental group was very dense and both the scores were 2 (FIG. 7). Inflammation score: The infiltration of lymphocytes in the gauze control group wasn't significant, and the wounds of the experimental group had small to medium lymphocyte infiltration. The endogenous in the experimental group was significant to the gauze control group (FIG. 7).

Example 9

Bacterial Preventing and Antiseptic Test

For the hydrogel structure (LexiDerm) of the present invention, the bacterial preventing and antiseptic effects were examined based on JIS L1902:2008, the results were as Table 5 (strain: *Staphylococcus*) and Table 6 (strain: *Klebsiella pneumoniae*):

TABLE 5

| | | Result | |
|---|---|---|---|
| Test Article | | Control | LexiDerm |
| *Staphylococcus* ATCC 6538P | Bacterial planting concentration | 1.8 × 10$^5$ | 1.8 × 10$^5$ |
| | Ma [1] | 3.9 × 10$^4$ | — |
| | Mb [2] | 1.4 × 10$^7$ | — |
| | Mo [3] | — | 2.8 × 10$^4$ |
| | Mc [4] | — | <20 |
| | Proliferation value [5] | 2.6 | — |

TABLE 5-continued

| Test Article | Result | |
|---|---|---|
| | Control | LexiDerm |
| Antiseptic activity value [6] | — | 5.7 |
| Bactericidal activity value [7] | — | 3.3 |

\* The test base on JIS L1902:2008
[1] Ma = The amount of bacteria immediately after washing in the control group
[2] MB = The amount of bacteria 18 hours after culture in the control group
[3] Mo = The amount of bacteria immediately after washing in the experimental group
[4] Mc = The amount of bacteria 18 hours after culture in experimental group
[5] Proliferation value = logMb-logMa
[6] Antiseptic activity value = (logMb-logMa)-(logMc-logMo)
[7] Bactericidal activity value = logMa-logMc Source: TTRI Report 2010/07

TABLE 6

| Test Article | | Result | |
|---|---|---|---|
| | | Control | LexiDerm |
| Klebsiella pneumoniae ATCC 6538P | Bacterial planting concentration | $1.6 \times 10^5$ | $1.6 \times 10^5$ |
| | Ma [1] | $2.8 \times 10^4$ | — |
| | Mb [2] | $2.0 \times 10^7$ | — |
| | Mo [3] | — | $2.9 \times 10^4$ |
| | Mc [4] | — | <20 |
| | Proliferation value [5] | 2.9 | — |
| | Antiseptic activity value [6] | — | 6.0 |
| | Bactericidal activity value [7] | — | 3.2 |

\* The test base on JIS L1902:2008
[1] Ma = The amount of bacteria immediately after washing in the control group
[2] MB = The amount of bacteria 18 hours after culture in the control group
[3] Mo = The amount of bacteria immediately after washing in the experimental group
[4] Mc = The amount of bacteria 18 hours after culture in experimental group
[5] Proliferation value = logMb-logMa
[6] Antiseptic activity value = (logMb-logMa)-(logMc-logMo)
[7] Bactericidal activity value = logMa-logMc Source: TTRI Report 2010/07

What is claimed is:

1. A method of covering a circular wound, which is applying a dressing at a wound area by circular covering such that the dressing extends around the wound area, wherein the dressing comprising an inner layer and an outer layer and the dressing having two longitudinal side edges and two short side edges, wherein the inner layer and outer layer are aligned only at one short side edge, and the inner layer and the outer layer are not aligned at another short side edge and the two longitudinal side edges such that the outer layer is not in contact with the circular wound; the inner layer comprises a hydrogel layer and a meltblown nonwoven layer, and the outer layer comprises a polyurethane film and a pressure sensitive adhesive film, wherein part of the meltblown nonwoven layer and part of the hydrogel layer are laminated by UV curing to form an interpenetrating polymer network, and part of fibers of the remaining meltblown nonwoven layer are exposed and fit directly and stably with the pressure sensitive adhesive film, thereby laminating the inner layer and the outer layer as one piece, wherein the circular wound is a circumcision wound.

\* \* \* \* \*